United States Patent [19]

Hiraoka et al.

[11] Patent Number: 4,564,444
[45] Date of Patent: Jan. 14, 1986

[54] FILAMENTOUS MICROORGANISM DETECTOR AND AN APPARATUS WITH THE DETECTOR FOR CONTROLLING THE PROCESS USING MICROORGANISMS

[75] Inventors: Masakatsu Hiraoka, Uji; Kazushi Tsumura, Nagaokakyo; Kenji Baba, Hitachi; Shunsuke Nogita, Hitachi; Shunji Mori, Hitachi, all of Japan

[73] Assignee: Hitachi, Ltd., Tokyo, Japan

[21] Appl. No.: 634,536

[22] Filed: Jul. 26, 1984

[30] Foreign Application Priority Data

Jul. 28, 1983 [JP] Japan .................. 58-140423

[51] Int. Cl.$^4$ .................. C02F 3/20; C12M 1/36
[52] U.S. Cl. .................. 210/96.1; 210/614; 210/195.3; 356/72; 422/79; 435/43; 435/289; 435/291; 382/10; 382/6
[58] Field of Search .......... 210/614, 96.1, 626, 210/195.3, 202, 745; 382/6, 10; 358/107; 356/39, 72, 394; 435/43, 289, 291, 313–316; 422/79, 73

[56] References Cited

U.S. PATENT DOCUMENTS

| | | |
|---|---|---|
| 3,557,954 | 1/1971 | Welch .................. 210/96.1 |
| 3,558,255 | 1/1971 | Rose .................. 210/96.1 |
| 3,986,932 | 10/1976 | Brushwyler et al. .................. 210/614 |
| 4,130,481 | 12/1978 | Chase et al. .................. 210/614 |
| 4,197,088 | 4/1980 | Meserol et al. .................. 422/73 |
| 4,338,024 | 7/1982 | Bolz et al. .................. 356/39 |
| 4,339,799 | 7/1982 | Abele et al. .................. 382/6 |
| 4,341,632 | 7/1982 | Gregor et al. .................. 210/626 |
| 4,437,161 | 3/1984 | Anderson .................. 382/6 |

Primary Examiner—Benoit Castel
Attorney, Agent, or Firm—Antonelli, Terry & Wands

[57] ABSTRACT

A system for controlling a process utilizing filamentous microorganisms is disclosed. The amount of the microorganisms in a medium for growing the filamentous microorganisms is measured, and the control factors associated with the growth of the microorganisms in the medium are controlled on the basis of the measurement of the amount of microorganisms. In the process of measuring the amount of microorganisms, an optical image of a specimen of the medium is formed and scanned two-dimensionally to produce a series of brightness signals corresponding to the brightness distribution of the optical image. The level of the brightness signal is used to determine the amount of the microorganisms contained in the medium.

6 Claims, 20 Drawing Figures

FILAMENTOUS MICROORGANISM DETECTOR AND AN APPARATUS WITH THE DETECTOR FOR CONTROLLING THE PROCESS USING MICROORGANISMS

BACKGROUND OF THE INVENTION

1. FIELD OF THE INVENTION

The present invention relates to a filamentous microorganism detecting apparatus and an apparatus combined with the detecting apparatus for controlling a process utilizing microorganisms, or more in particular to a control apparatus for a process utilizing microorganisms which can maintain environmental conditions suitable for culturing the microorganisms high in settleability.

2. DESCRIPTION OF THE PRIOR ART

A process utilizing microorganisms, in which the metabolic function and growth function of microorganisms are used, is applied to the production of useful materials or disposal of hazardous materials. In such a process, the control of microorganisms is very important since microorganisms play the main role in reactions.

In the sewage treatment process, for instance, microorganisms called activated sludge are cultured in the system, and the organic material in the sewage is removed by use of this activated sludge. The activated sludge is separated in a settling tank and circulated for reuse to treat the sewage. If the control of the activated sludge microorganisms is improper, the settleability of the activated sludge flock (agglomerate of activated sludge) is deteriorated and flows out of the system.

This is attributable to an abnormal growth of filamentous fungi such as sphaerotilus in the microorganisms of the activated sludge. This abnormal growth, in turn, is generally caused by an improper value of (1) the dissolved oxygen concentration in the aeration tank or (2) the load of organic materials. Upon detection of the abnormal growth of filamentous fungi or a sign thereof, therefore, the process must be regulated to make the factors (1) and (2) above proper. The detection of filamentous fungi, however, requires a visual decision under microscope or measurement with curvimeter of the amount of filamentous fungi based on the photography by a skilled operator. The decision takes a long time, and if made visually, is variable depending on the operator's subjective point of view, leading to a great error.

As a result, it is actually impossible to set a control target of the dissolved oxygen concentration or the load of organic materials for the process. The control operation is thus unavoidably effected only after the abnormal growth of filamentous fungi, and the abnormal growth cannot be prevented in the initial stage of detection of filamentous fungi. The resulting disadvantages are the deterioration of the quality of the treated water or part of the activated sludge flowing out.

Another process using microorganisms involves the production of a useful material such as an antibiotic from filamentous microorganisms including bactriomycota, ascomycota, actinomycota or bacidiomycota. In the penicillin production process, for example, penicillium chrysogenum or like is cultured, while streptomyces griseus or like is cultivated in the streptomycin production process to obtain an antibiotic. The growth rate of the filamentous fungi of an antibiotic and the substrate consumption rate are known to be greatly affected by the agitation force. This is primarily caused by an increased viscosity of the broth or culture solution of filamentous fungi which the oxygen supply to the filamentous fungi and the oxygen absorption rate thereof.

Due to the difficulty of measuring the amount of filamentous fungi in the culture tank, on the other hand, it is impossible to measure the growth rate of the filamentous fungi. Generally, the amount of filamentous fungi is calculated as the weight of a solid obtained after centrifugal separation and drying processes. In this method, however, the measurement takes at least three hours, making it impossible to improve the production efficiency by maintaining proper oxygen supply.

SUMMARY OF THE INVENTION

Accordingly, it is an object of the present invention to provide an apparatus for detecting the amount of filamentous microorganisms in a culture tank rapidly by simple means.

Another object of the present invention is to provide an apparatus for controlling a process using microorganisms, in which the amount of filamentous fungi in a culture tank or an aeration tank is detected by a filamentous microorganism detector such as mentioned above, and on the basis of the detection, the metabolism and growth of the filamentous fungi are controlled to attain an optimum amount of the filamentous fungi in the culture tank or aeration tank thereby to improve the production efficiency and the process maintenance and controllability.

According to one aspect of the present invention, there is provided a filamentous microorganism detecting apparatus comprising means for scanning two-dimensionally an optical image of a specimen sampled from a medium containing the filamentous microorganisms to be measured and generating a series of electrical signal corresponding to the brightness distribution of the specimen image, means for extracting an electrical signal associated with the specific characteristic of the filamentous microorganism out of the electrical signal generated by the scanning means, and operating means for counting the number of the electrical signals extracted and thereby calculating the amount of the filamentous microorganisms contained in the medium from the count.

According to another aspect of the present invention, there is provided an apparatus for controlling a process using the activity of the filamentous microorganisms in a medium, capable of regulating the amount of the filamentous microorganisms in the medium by controlling predetermined control factors, which comprises means for determining the amount of the filamentous microorganisms in the medium from a specimen sampled from the medium, a sensor for detecting a specific factor associated with the condition of the medium which is a function of the amount of the filamentous microorganisms contained in the medium, and generating an output signal representing the value of the condition factor, means for comparing the output signal of the sensor with a target of the condition factor, and means for controlling the condition factor in accordance with the result of comparison.

BRIEF DESCRIPTION OF THE DRAWINGS

FIG. 17 is a characteristic diagram of oxygen concentration.

FIGS. 18 and 19 are diagrams showing configurations of other embodiments of the present invention respectively.

FIG. 20 shows the characteristic of a carbon dioxide gas production rate.

DESCRIPTION OF THE PREFERRED EMBODIMENTS

Figure 1:
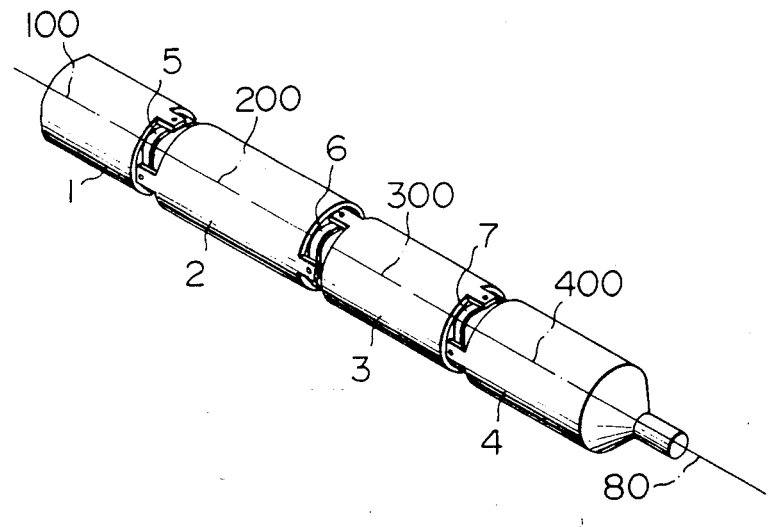
FIG. 1 is a diagram showing a configuration of a process control circuit according to an embodiment of the present invention.

A process control system according to the present invention as applied to a sewage treatment process will be explained below with reference to FIGS. 1 to 8. FIG. 1 is a schematic diagram showing a sewage treatment process.

The sewage from a sewage receiving tube 20 and the return sludge from a return sludge tube 30 flow into an aeration tank 10. A blower 40, on the other hand, supplies air through an air tube 50 from an air diffuser 60 to the aeration tank 10. The return sludge and the sewage are agitated and mixed in the aeration tank 10. The return sludge, that is, the activated sludge absorbs oxygen from the air and decomposes part of the soluble organic materials in the sewage by aerobic metabolism into carbon dioxide and water, and the remaining part of the organic materials taken in by microorganisms is used for growth of microorganisms of the activated sludge. The mixture of the activated sludge and sewage is led to a settling tank 70, where the microorganisms of the activated sludge settle by gravity. The treated water from which the organic materials have been removed, on the other hand, is supplied through a processing tube 80 and released through a sterilization step by using chlorine not shown. The activated sludge settled in the settling tank 70 is extracted from a sludge discharge tube, and the part thereof representing growth is discharged by an excess sludge pump 100 as an excess sludge, while most of the remaining activated sludge is returned to the aeration tank 10 by a return sludge pump 110 and the return sludge tube 30.

The activated sludge in the aeration tank 10 is sampled by a sampling tube 120, led to a filamentous fungus detecting apparatus 130, and then supplied to a filamentous fungus amount setting means 140 for measuring the amount of filamentous fungi f, where the target value f* of the amount of filamentous fungi is set. The difference $\Delta f$ between f and f* is applied to regulation meters 150, 151.

$$\Delta f = f - f^* \tag{1}$$

The regulation meters 150, 151 control the blower 40, the return sludge pump 110 and the excess sludge pump 100 in accordance with the magnitude of the difference signal $\Delta f$ as mentioned later.

Now, the filamentous fungus detecting apparatus 130 will be described before the operation of the system shown in FIG. 1.

Figure 2:
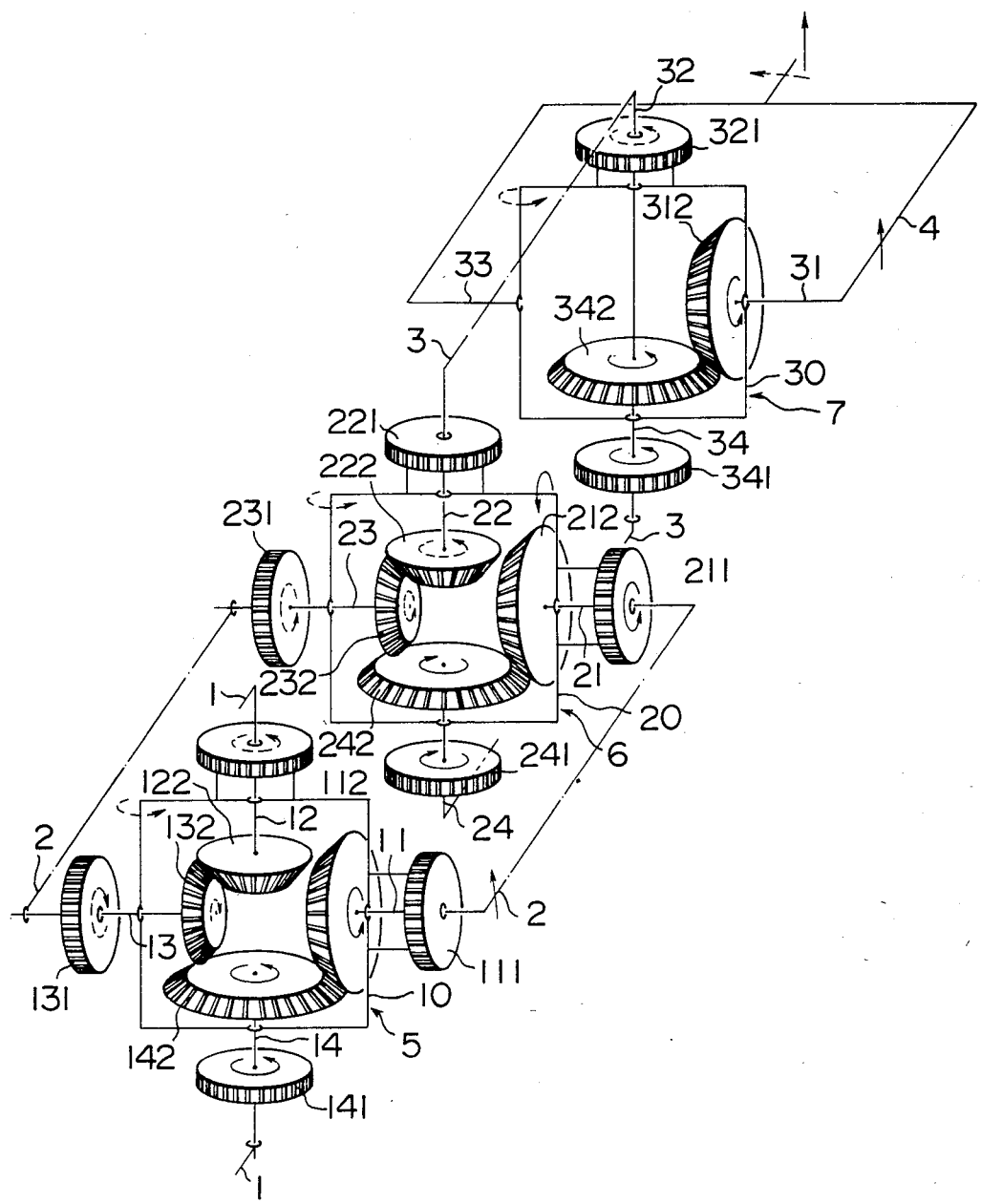
FIG. 2 is a block diagram showing a configuration of a filamentous microorganism detecting apparatus according to the present invention.

FIG. 2 shows a construction of a filamentous fungus detecting apparatus 130 according to the present invention.

A mixture sampled through a sampling tube 120 is led from a pump 131 to a detection plate 132 and then discharged from a discharge tube. The waste solution thus discharged is usually returned to the aeration tank 10. An observation means 133 such as optical microscope is arranged in small spaced relationship above the detection plate 132. The detection plate 132 is preferably thin enough to focus the optical microscope. According to a normal method of observation under optical microscope, a sampled specimen is dropped on the slide glass and may be observed with a cover glass thereon. In the bright field of the optical microscope, the object of observation appears black and the solution white.

A scanning device 134 scans the specimen image from the observation means 133 two-dimensionally to produce a series of brightness signal corresponding to the brightness distribution of the specimen image. The scanning device 134 is, for example, a vidicon camera including an array of CCD elements disposed in 256 lines and 256 rows, by which a specimen image is divided into 256×256 picture elements and scanned two-dimensionally by a well-known method thereby to produce a series of brightness signals representing the brightness of respective picture elements.

Figure 3:
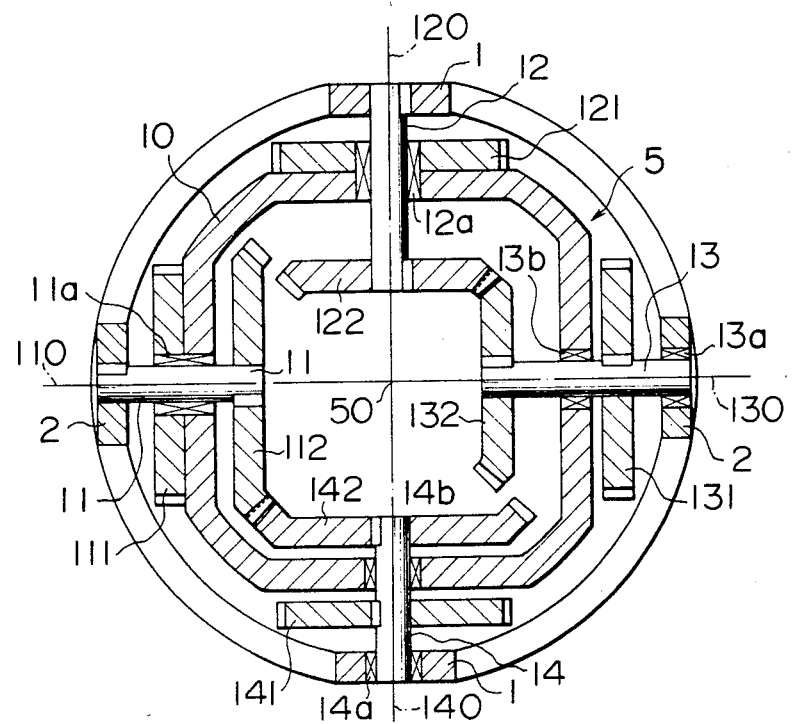
FIG. 3 shows an example of a microorganism image.

An A/D converter 135 converts the brightness signal from the vidicon camera 134 into a digital signal. FIG. 3 shows an example of the specimen image obtained from the observation device. Character Z designates an agglomerate of zoogloea microorganisms high in cohesiveness and settleability among the activated sludge flocks, and character F filamentous fungus low in settleability. Character B designates the background, that is, the solution. The hatched portion of the microorganism agglomerate Z indicates a black appearance.

The vidicon camera 135 first scans this object along line 1 in the direction X, and sequentially moving, line by line, along the Y axis, covers a frame of the specimen image by completing the scanning of the 256 lines along X direction, thus producing a series of signals representing the particular frame.

Figure 4:
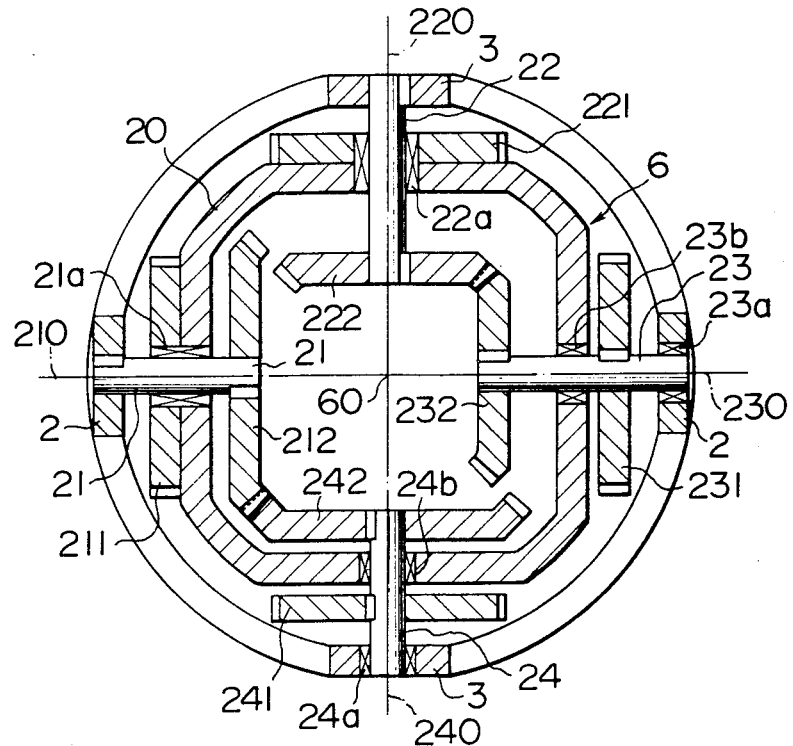
FIG. 4 illustrates the brightness level of a microorganism image.

FIG. 4 shows a brightness signal produced by the scanning along the line A—A in FIG. 3. As seen from FIG. 4, the liquid portion B is bright, whereas the flock portion Z appears black and therefore is low in brightness. In the dark field of observation under microscope, on the other hand, the object of observation appears white and the liquid white, so that the brightness signal distribution in FIG. 4 is reversed in brightness.

A threshold setting circuit 136 in FIG. 2 is provided for setting a brightness level Sl higher than the brightness of the flock portion Z but lower than that of the filamentous fungi F and a brightness level Sh higher than the brightness of the filamentous fungi F but lower than that of the liquid portion B in order to extract the filamentous fungi F selectively. The extractor circuit 137 extracts the picture elements of the filamentous fungi F in response to set signals Sl and Sh and a brightness signal Sij for the picture element at line i, row j. Specifically, assuming that the picture element of the filamentous fungus F at line i, row j is fij, signals representing the picture elements corresponding to the filamentous fungi F are raised to "1" according to the rules expressed below.

When $Sl \leq Sij \leq Sh$, $fij=1$ (2)

When $Sij < Sl$ or $Sij > Sh$, $fij=0$ (3)

Figure 5:
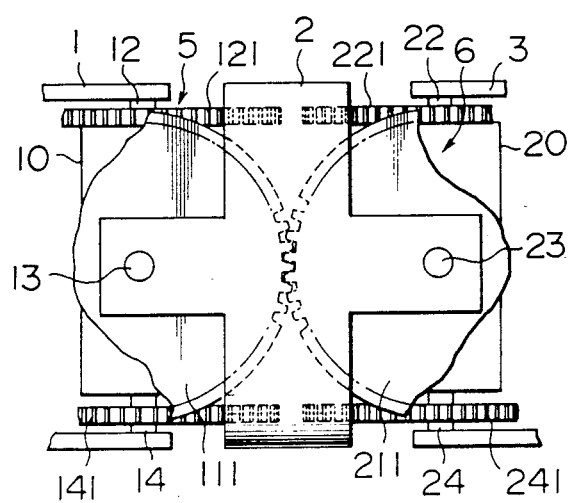
FIG. 5 is a diagram showing an example of a digitized brightness level.
Figure 6:
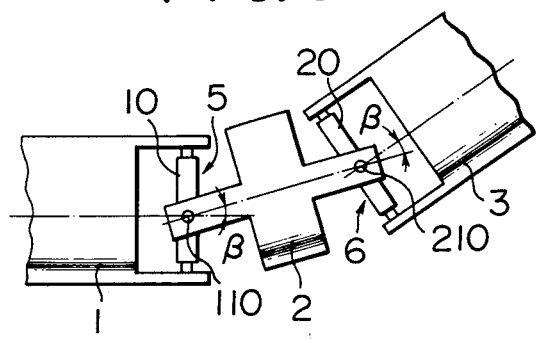
FIG. 6 shows an image of filamentous fungi.

For this purpose, the extractor circuit 137 includes a comparator 140 for comparing the brightness signals Sij and Sh representing the brightness levels of the picture elements and generating a high-level signal "1" when $Sij \leq Sh$, a comparator 141 for comparing Sij and Sh and generating a high-level signal "1" when $Sij \geq Sh$, and an AND gate 142 for producing a signal "1" when the output signals of both the comparators 140 and 141 are "1". An example of the process of FIG. 4 is shown in FIG. 5, and an example of the image of filamentous fungi F extracted from FIG. 3 is shown in FIG. 6. Equations (2) and (3) indicate the case of bright field of view, in which the inequality signs are all reversed in the case of dark field of view.

The operation circuit 138 is for counting the "1" levels of the picture element signal fij contained in a frame extracted by the extractor circuit 137 and producing the amount of filamentous fungi from the count. Specifically, the amount of filamentous fungi is determined from the equation below.

$$fv = \sum_i \sum_j fij \quad (4)$$

In view of variations in the amount of filamentous fungi fv from one frame to another, it is preferable to calculate the amount of filamentous fungi fv for a plurality of frames and to obtain a mean value thereof. A mean value $\overline{fv}$ for n frames is given by the equation below.

$$\overline{fv} = \sum_{k=1}^{n} fvk/n \quad (5)$$

The extractor circuit 138 includes a counter 145 for counting signals "1" from the AND gate 142 and a latch circuit 146 for latching the content of the counter 145. Also, a counter 144 is provided for counting the output from the vertical sync signal generator circuit 143 of the vidicon 134 in order to set and reset the counter 145. The counter 144 counts the sync signals generated at the start time point of scanning of each frame of each specimen image and produces a reset signal when the count reaches n+1. In response to the reset signal, the latch circuit 146 latches the prevailing content of the counter 145. The same reset signal is used also for resetting the counters 144 and 145 through a delay circuit 147. The delay circuit 147 is for resetting the counters 144 and 145 after complete latching of the content of the counter 145 by the latch 146. The latch 146 includes a divider circuit for calculating fv/n and the output thereof represents $fv/n = \overline{fv}$.

Figure 7:
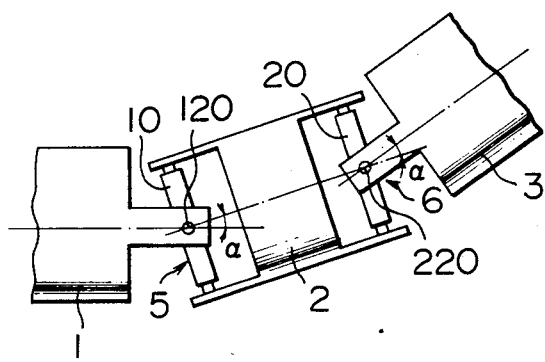
FIG. 7 is a detection characteristic diagram of a filamentous fungus detecting apparatus.

On the basis of this concept, the inventors measured by using a curvimeter the actual total length L of the filamentous fungi in an activated sludge mixture obtained from the aeration tank of the sewage treatment process and compared the resulting measurement with the amount of filamentous fungi fv detected by the filamentous fungus detecting apparatus 130. As a consequence, the relation as shown in FIG. 7 was obtained. In the drawing, the circles represent values detected by the filamentous fungus detecting apparatus 130. This relation is expressed by equation (6) below.

$$f = a \cdot \overline{fv} + b \quad (6)$$

where a and b are constants.

In this way, the absolute value of the amount of filamentous fungi can be measured quickly and objectively by image processing.

Figure 8:
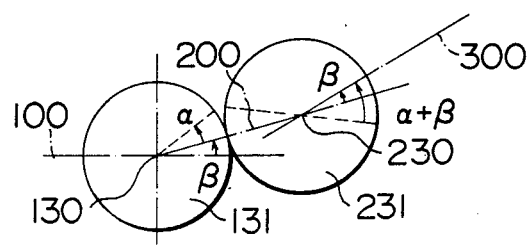
FIG. 8 shows a characteristic of a sewage treatment process.

Filamentous fungi are liable to grow more at a low concentration of dissolved oxygen. On the other hand, an appropriate range of load of organic materials exists as shown in FIG. 8. The load of organic materials is given as F/M, where F is the amount of inflowing organic materials, and M the amount of the solid of activated sludge in the aeration tank. In FIG. 8, the load of organic materials F/M is plotted along the abscissa and the sludge value index SVI along the ordinate. A larger SVI indicates a greater amount of filamentous fungi. As seen from FIG. 8, there is an optimum value of F/M minimizing SVI, and an increase or decrease of F/M therefrom increases SVI. If the increase in the amount of filamentous fungi is to be prevented, therefore, the dissolved oxygen concentration should be increased while at the same time maintaining the load of organic materials at proper value.

In the system of FIG. 1, the blower 40 is operated by the regulator 150 to control the dissolved oxygen concentration, while the return sludge pump 110 and the excess sludge pump 100 are operated by the regulator 151 to control the load of organic materials. The amount of sludge discharged by the excess sludge pump 100 generally accounts for 1 to 2% of the amount of inflow sewage. These control operations will be described below in detail.

Figure 9:
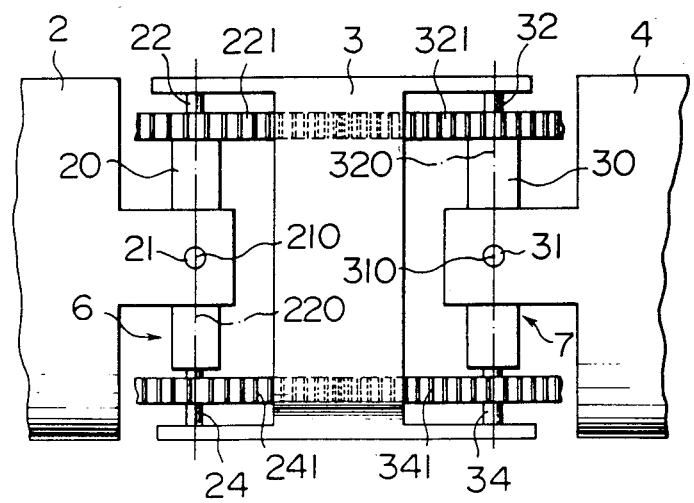
FIG. 9 is a diagram showing a part of the circuit of FIG. 1 in detail.

FIG. 9 shows a specific example of the control of dissolved oxygen concentration for the system shown in FIG. 1.

Figure 10:
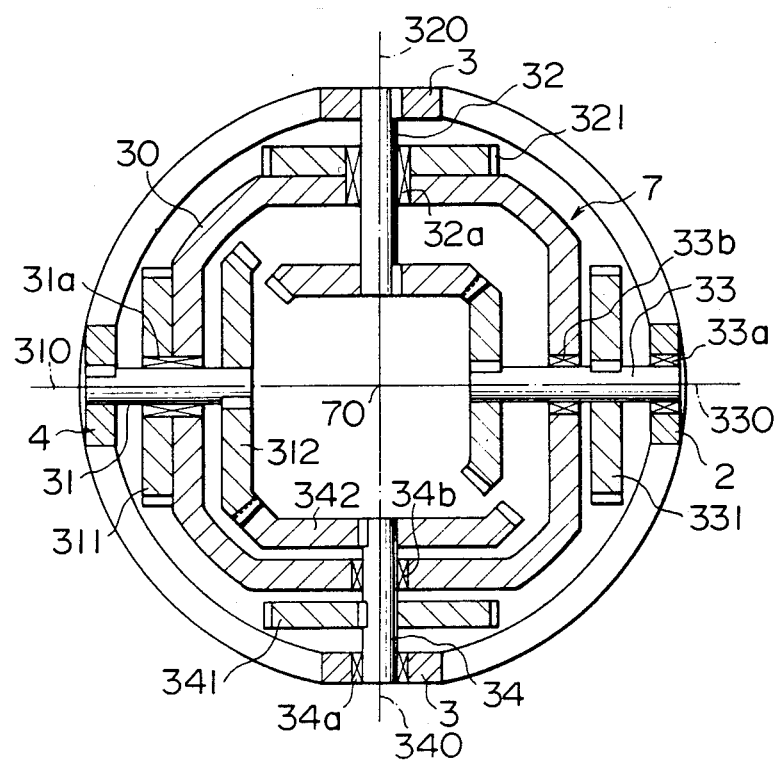
FIG. 10 shows a characteristic of the target value of a dissolved oxygen concentration.

A dissolved oxygen concentration target operation circuit 160 is supplied with an error signal $\Delta f$ between a measurement signal f of the amount of filamentous fungi and a target f* set in a filamentous fungus amount setter 140 and produces a dissolved oxygen concentration target DO* as shown in FIG. 10. The target DO* has an upper limit DOmax and a lower limit DOmin to prevent excessive aeration and to secure a minimum DO level. The regulator 150 is supplied with an error $\Delta$DO between the dissolved oxygen concentration target DO* and the measurement DO detected at the dissolved oxygen concentration meter 170. The error ΔDO is calculated by the equation below.

$$\Delta DO = DO - DO^* \quad (7)$$

The regulator meter 150 operates the blower 40 in such a way that the dissolved oxygen concentration is reduced by reducing the amount of aeration when the concentration error ΔDO is positive. This is achieved, for example, by reducing the rotational speed of the blower 40. In the case where the concentration error ΔDO is negative, on the other hand, the blower 40 is operated to increase the dissolved oxygen concentration by increasing the amount of aeration. In view of the fact that the dissolved oxygen concentration DO actually changes with various other factors and measurements thereof are unstable depending on the measuring conditions, however, the blower 40 should preferably be subjected to PI control with an integration component added to the proportional component of ΔDO.

Since the increase or decrease in the amount of filamentous fungi due to growth or extinction does not occur suddenly, the dissolved oxygen concentration target DO* may be changed once or several times a day.

By changing the dissolved oxygen concentration in this way, the abnormal growth of filamentous fungi is prevented.

Figure 11:
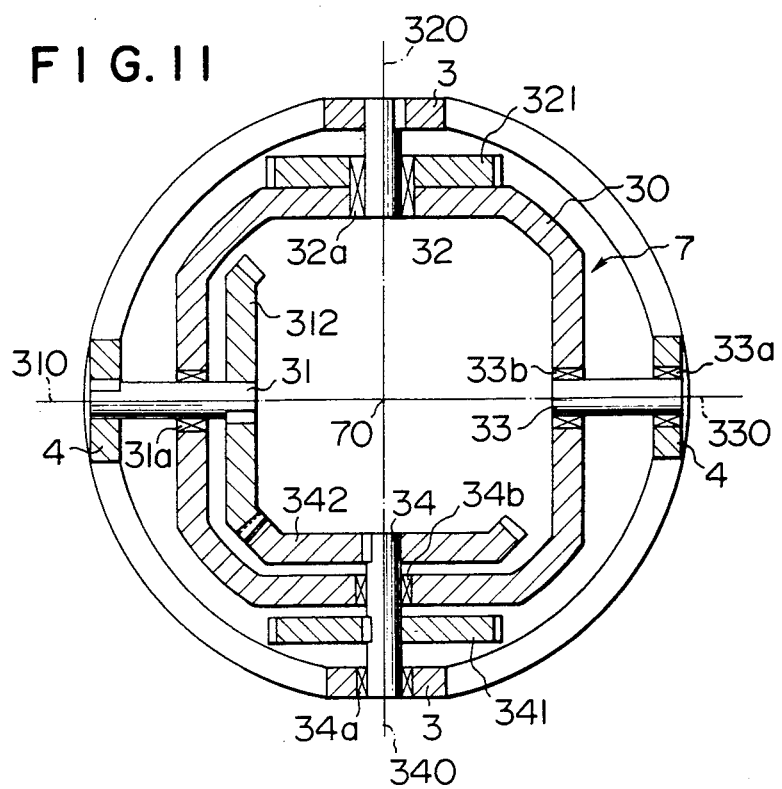
FIG. 11 is a diagram showing another detailed configuration of a part of the circuit shown in FIG. 1.

FIG. 11 shows a specific example of control of the organic load F/M illustrated in FIG. 1.

The amount of inflowing organic materials cannot generally be controlled, and therefore the amount of solid activated sludge in the aeration tank is controlled. The amount of solid activated sludge in the aeration tank is given by the equation below.

$$Mt = Vl \times Ma \quad (8)$$

where

Mt: Amount of solid activated sludge in aeration tank
Vl: Amount of mixture in aeration tank
Ma: Concentration of activated sludge in aeration tank (hereinafter called sludge concentration).

The amount of mixture in the aeration tank Vl remains constant, and therefore the amount Mt of the solid activated sludge can be controlled by controlling the sludge concentration Ma. The concentration of activated sludge in aeration tank Ma, on the other hand, is normally controlled by controlling the amount of return sludge. Since the range of control of the return sludge is limited, however, the amount of excess sludge is also controlled. Generally, the return sludge pump is operated continuously so that the amount of return sludge is controlled by regulating the pump speed, while the amount of discharge is controlled by adjusting the operating time of the excess sludge pump which is operated intermittently at a rate of several times an hour.

Specific explanation will be made. The activated sludge in the aeration tank 10 is introduced through a sampling tube 120 to the filamentous fungus detecting apparatus 120 and detected. Specifically, the amount of filamentous fungi $\overline{fv}$ is obtained to produce the filamentous fungus amount signal f as explained above. An overload condition occurs if the detection signal f is larger than the target f* and the error of filamentous fungus amount Δf is very positive. In this case, the sludge concentration Ma is increased to reduce the organic load F/M. The sludge concentration Ma can be increased by increasing the rotational speed of the return sludge pump 110 to increase the amount of return sludge. As an alternative, the amount of excess sludge may be reduced to increase the amount of activated sludge in the process. The amount of excess sludge, on the other hand, can be reduced by shortening the operation time of the excess sludge pump 100.

In the case where the filamentous fungus error Δf is negative, by contrast, the rotational speed of the return sludge pump 110 is reduced or the operation time of the extraneous sludge pump 100 is lengthened.

Figure 12:
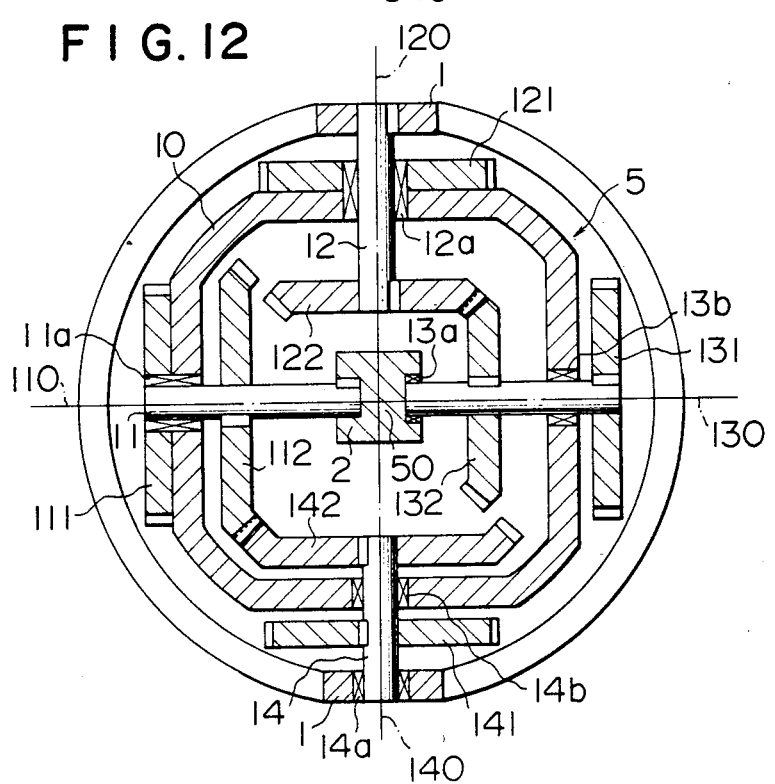
FIG. 12 is a diagram showing a characteristic of the target value of a sludge concentration.

Specific methods of these operations will be described. A sludge concentration calculation circuit 190 is supplied with an error signal Δf and calculates a sludge concentration target Ma* in the relation shown in FIG. 12. In the manner shown in FIG. 12, an upper limit $Ma_{max}$ and a lower limit $Ma_{min}$ of the target Ma* are set. Generally, the sludge concentration Ma detected by a sludge concentration meter with light transmission or light reflection type 200 is compared with the target Ma*, and the resulting error ΔMa is applied to the regulator 151.

$$\Delta Ma = Ma - Ma^* \quad (9)$$

When the sludge concentration error signal ΔMa is positive, the regulator 151 reduces the rotational speed of the return sludge pump 110 or lengthens the operation time of the excess sludge pump 100 in a manner to reduce the sludge concentration Ma. When the sludge concentration error ΔMa is negative, on the other hand, the rotational speed of the return sludge pump 110 is increased or the operation time of the excess sludge pump 100 is shortened to increase the sludge concentration Ma.

In view the fact that the growth or extinction of the filamentous fungi or the change of the microorganic phase in the activated sludge does not occur suddenly, a predetermined effect is achieved by changing the operation of the return sludge pump 110 or the excess sludge pump 100 only about once a day.

Figure 13:
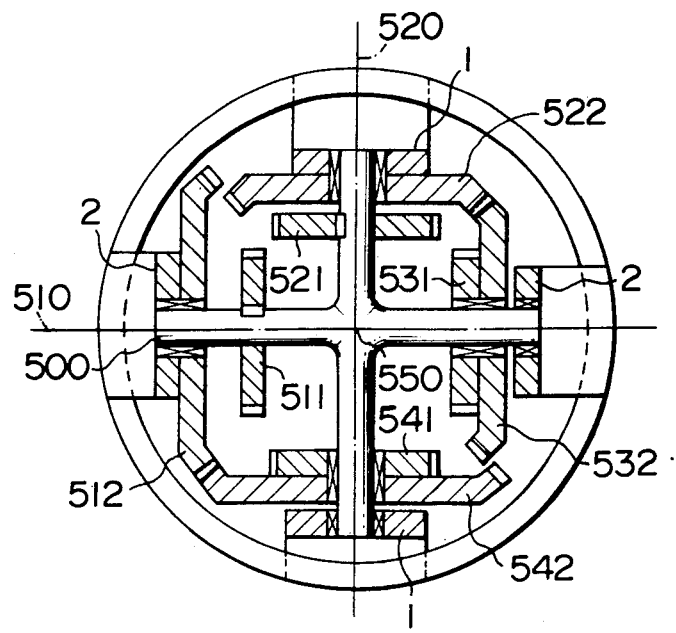
FIG. 13 shows a configuration of a process control apparatus according to another embodiment of the present invention.

If the amount of inflowing sewage is too small in controlling the sludge concentration, the organic load is so small that the filamentous fungi are liable to grow. In such a case, the amount of the inflowing sewage is detected as shown in FIG. 13, and if the detection value is small, the operation of the return sludge pump 110 or the excess sludge pump 100 is reversed in direction. Specifically, when the sludge concentration error ΔMa is positive, the rotational speed of the return sludge pump 110 is increased or the excess sludge pump is started less frequently.

In this way, the organic load can be controlled by changing the sludge concentration Ma, thus making it possible to avoid abnormal growth of filamentous fungi.

FIG. 13 shows an embodiment of the present invention as applied to a penicillin production process.

A culture broth 310 containing penicillin-producing microorganisms such as penicillium chrysogenum which is a filamentous fungus is cultured under aerobic conditions in a fermentor 300. Oxygen must be supplied to maintain an aerobic condition. Oxygen or a gas-containing oxygen is supplied from an oxygen supply 320 by a compressor 330 through a control valve 340 to the fermentor 300 under pressure. The pressurized gas is supplied from an air diffuser 350 and dissolved into the culture broth 310. The oxygen dissolved in the culture broth 310 is consumed by the penicillion-producing filamentous fungi (hereinafter called merely as the filamentous fungi). The filamentous fungi grow aerobically with oxygen on the one hand and produces penicillin as a product by aerobic metabolism on the other hand.

In order to promote the gas-liquid contact between the supplied oxygen and the culture broth and the absorption of the dissolved oxygen into the filamentous fungi, the agitation vanes are driven by a motor 360 to stir the culture broth 310. The motor 360 also drives the defoaming vanves 380 to collapse the bubbles generated on the surface of the culture broth.

Figure 14:
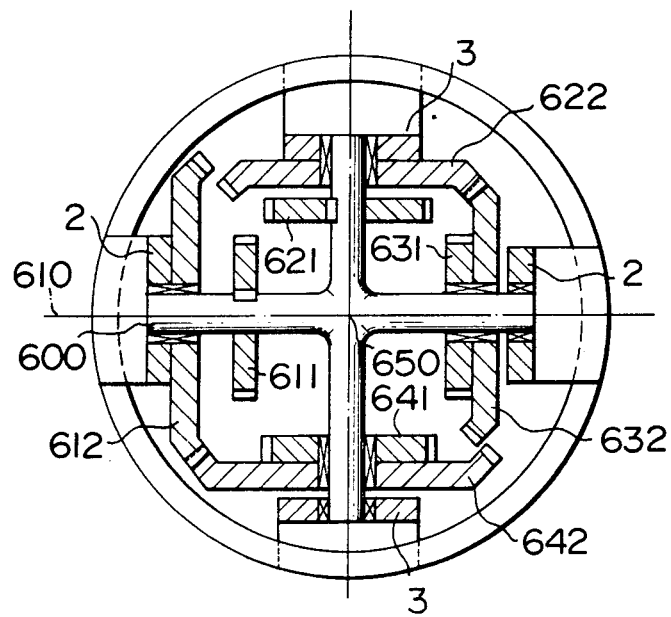
FIG. 14 is a diagram showing an image of filamentous fungi.
Figure 15:
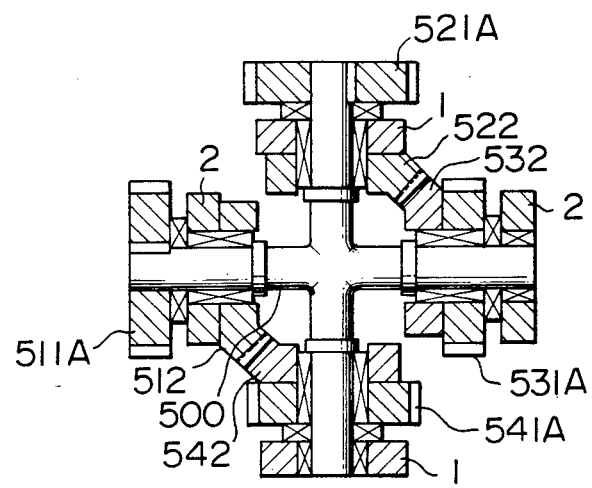
FIG. 15 is a diagram showing the brightness level of the filamentous fungi.

A small amount of the culture broth 310 is collected as a sample from this culture tank 300 by a sampling tube 390, and the amount of filamentous fungi f is measured at a filamentous fungus detector 400. The filamentous fungus detector 400 has a construction similar to the filamentous fungus detector 130 shown in FIG. 2. An enlarged image of the sample is obtained under an optical microscope 133, and scanned two-dimensionally by a vidicon camera 134 thereby to produce a series of brightness signal. An A/D converter 135 converts the brightness signal produced by the vidicon camera 134 into a digital signal. FIG. 14 shows a sample containing the penicillin-producing filamentous fungi (in the bright field of view), and FIG. 15 illustrates the brightness signal produced by scanning along line A—A'. As will be seen, the brightness of the picture elements associated with the filamentous fungi is lower than that of the liquid portion. In the case where the sample is observed in the dark field of view, by contrast, the brightness distribution is reversed. A threshold setting circuit 136 is for setting a threshold value of brightness for extracting the filamentous fungi F. Assuming that the brightness level of the liquid portion is Sb, a threshold level is set at Sl lower than Sb taking noises into consideration, so that a brightness signal lower than Sl indicates the existence of filamentous fungi. Sl is obtained from the equation below.

$$Sl = a \cdot Sb \quad (10)$$
($a$: Constant)

The constant a takes a value of about 0.9, for example.

The extractor circuit 137 picks up the picture elements fij alone representing the existence of filamentous fungi from the brightness signal Sij of the picture elements on line i, row j received from the A/D converter 135 on the basis of the threshold value Sl set by the setting circuit 136. The picture elements fij are picked up in the manner mentioned below.

When Sij≦Sl, fij=1  (11)

When Sij>Sl, fij=0  (12)

The equations (11) and (12) above concern the bright field of view, the unequality signs being reverse in the case of a dark field of view.

In this embodiment, an agglomerate which may be formed by filamentous fungi is still considered as filamentous fungi. The operation circuit 138 in FIG. 2 adds the signal fij of the extractor circuit 137 by equation (4) and produces the amount of filamentous fungi fv. A mean value $\overline{fv}$ of the amount of filamentous fungi is obtained from the equation (5).

In this manner, the filamentous fungus detector 400 computes the amount of filamentous fungi $\overline{fv}$ and produces a signal f representing the amount of filamentous fungi.

On the other hand, the oxygen concentration $O_{2in}$ of the supplied gas is measured by an oxygen concentration meter 431, and similarly, the oxygen concentration $O_{2out}$ of the exhaust gas is measured by an oxygen concentration meter 430. Let the amount of the supplied gas be Qg, and the oxygen absorption rate $A_{O2}$ in the fermentor 300 is given as $$A_{O2} = Qg \cdot (O_{2in} - O_{2out}) \quad (14)$$

An oxygen absorption rate calculation circuit 450 effects the calculation of equation (14) in response to detection signals $Q_{2in}$ and $Q_{2out}$ of the oxygen concentration meters 430 and 431. In the case where the oxygen concentration $Q_{2in}$ of the supplied gas is constant such as when air is used, the oxygen concentration meter 431 is not required. In the event that the amount of supplied gas Qg undergoes a change, the amount of supplied gas Qg must be measured by a means not shown and must be taken into consideration.

An oxygen consumption rate calculation circuit 460 calculates the oxygen consumption rate $R_{O2}$ of the filamentous fungi by the equation shown below in response to the filamentous fungus amount signal f of the filamentous fungus detector 400 and the oxygen absorption rate signal $A_{O2}$ of the operation circuit 450.

$$R_{o2} = A_{o2}/(f \cdot Vb) \quad (14)$$
($Vb$: Amount of fermentation liquid)

A regulator 480 is supplied with the oxygen consumption rate error signal $\Delta R_{O2}$ between the oxygen consumption rate signal $R_{O2}$ of the operation circuit 460 and the target signal $R_{O2}{}^*$ of the oxygen consumption rate setting circuit 470. The oxygen consumption rate error $\Delta R_{O2}$ is computed by the equation below. The target $R_{O2}{}^*$ is determined by experiments.

$$\Delta R_{O2} = R_{O2} - R_{O2}{}^* \quad (15)$$

Figure 16:
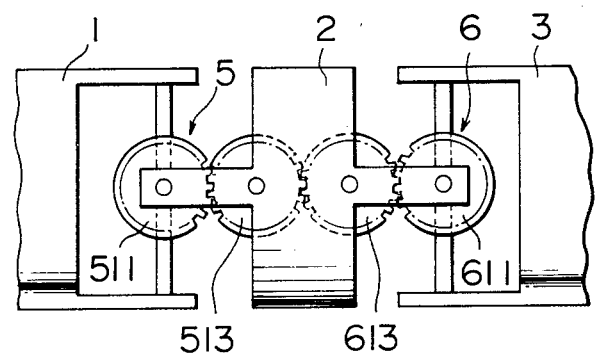
FIG. 16 shows a characteristic of motor r.p.m.

In accordance with the error signal $\Delta R_{O2}$ shown by equation (15) above, the regulator 480 controls first the agitation force and then the amount of supplied oxygen. When the error $\Delta R_{O2}$ is positive, the motor 360 is slowed down by the amount corresponding to the positive value, while if the error $\Delta R_{O2}$ is negative, the rotational speed of the motor 360 is increased by an amount corresponding to the negative value. In controlling the rotational speed of the motor 360, an excessive agitation may damage the microorganisms while an excessively slow agitation makes it difficult to produce a dead space. In order to avoid such an inconvenience, an upper limit $r_{max}$ and a lower limit $r_{min}$ are set on the rotational speed r of the motor 360 as shown in FIG. 16.

When the rotational speed r exceeds the upper limit $r_{max}$ or drops below the lower limit $r_{min}$ as a result of the speed changing operation of the motor 360, the amount of oxygen supply is adjusted. The regulator 480 is supplied with the rotational speed signal r of the motor 360, and when the upper limit $r_{max}$ or the lower limit $r_{min}$ is exceeded, stops the speed control of the motor 360, and adjusts the amount of oxygen supplied from the oxygen supply 320. The amount of supplied oxygen is thus adjusted by controlling the rotational speed of the compressor 330 and/or the opening rate of the control valve 340.

The oxygen supply 320 is constructed of, for example, a pressure swing adsorption device (PSA) including an adsorption column containing an adsorbent such as zeolite into which air is introduced, whereby the pressure in the column is regulated and the amount of $N_2$ adsorption is controlled thereby to control the oxygen concentration and produce an oxygen-rich gas. In the manner shown in FIG. 17, the oxygen concentration is normally maintained at 50% by volume, and when the oxygen consumption rate error $\Delta R_{O2}$ becomes positive, the oxygen concentration of the supplied gas $O_{2in}$ is reduced proportionately according to the positive value. If the oxygen consumption rate error $\Delta R_{O2}$ is negative, by contrast, the oxygen concentration $O_{2in}$ is increased proportionately according to the negative value. In FIG. 17, the lower limit 20% of the oxygen concentration $O_{2in}$ provides only an example in view of the oxygen content of 20% of the air.

The oxygen absorption rate of the culture broth increases with the rotational speed of the motor 360, the amount of gas supplied by the compressor 330 or the oxygen concentration of the supplied gas. In this way, the oxygen absorption rate and the oxygen consumption rate can be manipulated, thereby making it possible to maintain a high growth ability of filamentous fungi and a high production ability of antibiotics.

In the embodiment of FIG. 13, the dissolved oxygen concentration of the culture broth 310 can be properly controlled by using the measurement of the dissolved oxygen concentration of the culture broth 310.

The metabolic ability of microorganisms in aerobic culture can be controlled not with the $O_2$ consuming rate but with the carbon dioxide production rate as an index. Also, in the anaerobic culture without any oxygen supplied, the production rate of a gas such as methane gas or carbon dioxide gas provides a possible control index. A case of aerobic culture will be explained below.

An embodiment using the carbon dioxide gas production rate as a control index is shown in FIG. 18.

In FIG. 18, the same reference numerals as in FIG. 13 designate the component parts equivalent to those in FIG. 13.

The carbon dioxide gas concentration $CO_{2out}$ in the exhaust gas of the culture tank 300 is measured by a carbon dioxide gas concentration meter 432. A carbon dioxide gas production rate calculation circuit 461 is supplied with the amount of filamentous fungi f from the filamentous fungus amount detector 400, the supplied gas flow rate Qg from the flowmeter 490 and the carbon dioxide gas concentration $CO_{2out}$ from the carbon dioxide gas concentration meter 432, and calculates the carbon dioxide gas production rate $R_{CO2}$ according to the equation below.

$$R_{CO2} = Qg \cdot CO_{2out}/(f \cdot Vb) \tag{16}$$

The carbon dioxide gas production rate target $R_{CO2}*$ set in the carbon dioxide gas production rate setter 470 is compared with a measurement $R_{CO2}$, and the error $\Delta R_{CO2}$ therebetween is calculated by the equation below.

$$\Delta R_{CO2} = R_{CO2} - R_{CO2}* \tag{17}$$

The regulator 480, which is supplied with this error signal $\Delta R_{CO2}$, manipulates the amount of supplied oxygen in the same manner as in the embodiment of FIG. 13. When the error of the carbon dioxide gas production rate $\Delta R_{CO2}$ is positive, the rotational speed of the motor 360 and the compressor 330 is reduced and the opening rate of the control valve 340 is lessened in a manner to reduce the amount of supplied oxygen, thus reducing the oxygen concentration of the oxygen supply 320, and vice versa.

In this way, the carbon dioxide production rate of the cultured filamentous fungi is maintained properly so that the metabolic ability of the filamentous fungus is maintained at high level, resulting in a higher production efficiency of useful materials.

Another embodiment of the present invention is shown in FIG. 19. The embodiment shown in FIG. 19 represents a specific example in which the fed-batch culture for adding substrate of filamentous fungus sequentially is applied to the present invention.

In FIG. 19, the same reference numerals as those in FIG. 18 designate the component elements equivalent to those in FIG. 18 respectively. The substrates 510 are stored in a substrate storage tank 500. The substrates 510 are supplied to the culture tank 300 through a substrate supply tube 520 by a substrate supply pump 530. The amount of substrate supplied by the substrate supply pump 530 is controlled according to the carbon dioxide gas production rate error $\Delta R_{CO2}$ in the same manner as in the embodiment of FIG. 18.

As shown in FIG. 20, the carbon dioxide gas production rate $R_{CO2}$ is proportional to the ratio F'/M' between the substrate amount F' and the filamentous fungus amount M' in the culture tank 300. In the case where the substrate concentration of the culture broth 310 is high relative to the amount of filamentous fungi in the fermentor 300, therefore, the carbon dioxide gas production rate $R_{CO2}$ is increased, with the result that the error $\Delta R_{CO2}$ becomes positive. In such a case, the amount of substrate supply is reduced until the error $\Delta R_{CO2}$ becomes zero, and when the error $R_{CO2}$ has reached zero, the substrate supply pump 530 is stopped. When the substrate concentration is low, by contrast, the carbon dioxide gas production rate $R_{CO2}$ is decreased and therefore the error $\Delta R_{CO2}$ becomes negative. In this case, the amount of substrate supply is increased by controlling the substrate supply pump 530, preferably by PI control process using the proportional and integration components of the error $\Delta R_{CO2}$.

Since the amount of substrate supply is controlled in such a manner that the carbon dioxide gas production rate $R_{CO2}$ reaches a target as mentioned above, the metabolic ability of the filamentous fungus can be maintained at high level. As a consequence, the efficiency of production of such metabolic materials as antibiotics can be maintained high.

Unlike in the embodiment of FIG. 19 where only the amount of substrate supply is controlled, both the amount of substrate supply and the amount of oxygen supply may be controlled as shown in the embodiment of FIG. 18. In the present invention for controlling the growth ability or metabolic ability by measuring the amount of filamentous fungi, a better process control system would be achieved if the pH or temperature which are factors affecting the metabolic and growth abilities is controlled in addition.

It will be understood from the foregoing description that according to the present invention, it is possible to measure the growth ability and the metabolic ability of filamentous fungus easily and rapidly by determining the amount of filamentous fungi involved in a process utilizing microorganisms by image processing. Further, the process utilizing microorganisms can be controlled in a manner to maintain these abilities properly. As a result, the efficiency of a process utilizing microorganisms is greatly improved.

We claim:

1. A system for detecting filamentous microorganisms in a medium containing additionally a flock portion, comprising means for forming an optical image of a specimen of the medium, scanning means for scanning said specimen image two-dimensionally and generating a series of electrical signals indicating brightness levels of scanned points on said specimen image, means for extracting from the electrical signals produced from said scanning means those electric signals indicating a predetermined range of the brightness levels which are lower than a predetermined upper limit representing the background brightness of the specimen image, but higher than a predetermined lower limit representing the brightness of the flock portion, and operation means for counting the electrical signals extracted and calculating the amount of the filamentous microorganisms contained in said medium from said count.

2. A system for detecting filamentous microorganisms according to claim 1, wherein said extracting means includes a threshold setting circuit for setting a lower limit threshold value and an upper limit threshold value, and means for comparing said electric signals produced by said scanning means thereby to produce a high level signal in response to each electric signal which is not higher than said upper limit threshold value and not lower than said lower limit threshold value and to produce a low level signal in response to each selected signal which is higher than said upper limit threshold value and the brightness signal level lower than said lower limit threshold value.

3. A system according to claim 1, wherein said extraction means includes a threshold setting circuit for setting a threshold value predetermined according to the characteristics of the filamentous microorganism to be measured, and means for generating a high-level signal in response to selected one of said brightness signals higher than and equal to said threshold value and generating a low-level signal in response to said brightness signal lower than said threshold value.

4. An apparatus for controlling a process utilizing the activity of filamentous microorganisms contained in a medium additionally containing a flock portion, the amount of said microorganisms being controlled by controlling at least a predetermined control factor, comprising means for determining the amount of filamentous microorganisms in said medium from a specimen sample from said medium, a sensor for detecting a specific condition factor associated with the condition of said medium providing a function of the amount of the filamentous microorganisms in said medium and generating an output signal representing the value of said condition factor, means for comparing the output signal of said sensor with a target value of said condition factor, and means for controlling said control factor in accordance with the result of said comparison wherein said means for determining the amount of filamentous microorganisms comprises means for forming an optical image of said specimen, scanning means for scanning said optical image two-dimensionally and producing a series of brightness signals indicating brightness levels of scanned points on said optical image, means for extracting from said brightness signals those brightness signals indicating a predetermined range of the brightness levels which are lower than a predetermined upper limit representing the background brightness of said optical image, but higher than a predetermined lower limit representing the brightness of the flock portion and means for counting the number of said extracted brightness signals thereby determining the amount of the filamentous microorganisms from said count.

5. A system for controlling a sewage treatment apparatus including an aeration tank having inlets receiving a flow of external sewage and a flow of air for mixing and agitating the received sewage and air and producing activated sludge by growth of filamentous fungi in the sewage, a settling tank connected to said aeration tank for receiving from said aeration tank a mixture containing the activated sludge treated in said aeration tank and settling said activated sludge, and return pipe means connected between said aeration tank and said settling tank for returning part of the activated sludge settled in said settling tank to said aeration tank, said sewage being treated by utilizing the activity of the filamentous fungi in said activated sludge additionally containing sludge flocks; said system comprising:

means for determining the amount of filamentous fungi in said aeration tank from a specimen of a mixture containing the filamentous fungi and sludge flocks in said aeration tanks;

a sensor for detecting the dissolved oxygen concentration of the mixture in said aeration tank;

means for determining a target value of the dissolved oxygen concentration of the mixture from the amount of filamentous fungi determined; and means for controlling the amount of air supplied to said aeration tank on the basis of the error of the detection value of said dissolved oxygen concentration as compared with said target value wherein said means for determining the amount of filamentous fungi comprises means for forming an optical image of said specimen, scanning means for scanning said optical image two-dimensionally and producing a series of brightness signals indicating brightness levels of scanned points on said optical image, means for extracting from said brightness signals those brightness signals indicating a predetermined range of the brightness levels which are lower than a predetermined upper limit representing the background brightness of said optical image, but higher than a predetermined lower limit representing the brightness of the sludge flocks and means for counting the number of said extracted brightness signals thereby determining the amount of the filamentous fungi from said count.

6. A system according to claim 5, further comprising means for controlling the amount of said return activated sludge on the basis of the error of said detection value of the dissolved oxygen concentration as compared with said target value.

* * * * *